(12) United States Patent
Hofmann et al.

(10) Patent No.: US 6,790,463 B2
(45) Date of Patent: Sep. 14, 2004

(54) USES OF TARGETED OXIDATIVE THERAPEUTIC FORMULATION IN ARTERIOSCLEROSIS

(76) Inventors: Robert F. Hofmann, 3105 Toro Ring, Austin, TX (US) 78746; Robert H. Carpenter, 1303 Pecan St., Bastrop, TX (US) 78602

( * ) Notice: Subject to any disclaimer, the term of this patent is extended or adjusted under 35 U.S.C. 154(b) by 0 days.

(21) Appl. No.: 09/822,773

(22) Filed: Mar. 30, 2001

(65) Prior Publication Data

US 2002/0177585 A1 Nov. 28, 2002

(51) Int. Cl.$^7$ .................. A61K 31/045; A61K 31/10; A61K 31/327; A61K 31/335; A61K 31/34; A61K 31/35; A61K 31/28; A61K 31/40; A61K 31/685; A61K 33/40

(52) U.S. Cl. .................. 424/613; 424/400; 424/450; 424/600; 424/614; 424/615; 424/616; 424/617; 424/630; 424/639; 424/646; 424/650; 424/681; 424/722; 514/78; 514/169; 514/170; 514/171; 514/182; 514/185; 514/226.2; 514/250; 514/251; 514/408; 514/410; 514/412; 514/414; 514/422; 514/452; 514/453; 514/454; 514/455; 514/463; 514/467; 514/675; 514/678; 514/680; 514/681; 514/682; 514/685; 514/686; 514/687; 514/688; 514/689; 514/690; 514/692; 514/708; 514/709; 514/714; 514/724; 514/729; 514/738; 514/739; 514/766; 514/970

(58) Field of Search .................. 424/400, 450, 424/600, 613–617, 630, 639, 646, 650, 681, 722; 514/182, 185, 226.2, 250, 251, 408, 410, 412, 414, 422, 452–455, 463, 467, 675, 678, 680–682, 685–690, 692, 708, 709, 714, 724, 729, 738, 739, 766, 970, 78, 169–171

(56) References Cited

U.S. PATENT DOCUMENTS

2003/0032677 A1 * 2/2003 Hofmann .................. 514/714

OTHER PUBLICATIONS

Chemical Abstracts 125: 9418 (1996).*
Chemical Abstracts 105:223647 (1986).*

* cited by examiner

*Primary Examiner*—John Pak
(74) *Attorney, Agent, or Firm*—Jackson Walker L.L.P.

(57) ABSTRACT

The use of a pharmaceutical formulation in treating coronary arteriosclerosis and a two-component pharmaceutical formulation. The pharmaceutical formulation contains peroxidic species or reaction products resulting from oxidation of an alkene, such as geraniol, by an oxygen-containing oxidizing agent, such as ozone; a penetrating solvent, such as dimithyl sulfoxide; a dye containing a chelated metal, such as hematoporphyrin; and an aromatic redox compound, such as benzoquinone.

26 Claims, No Drawings

USES OF TARGETED OXIDATIVE THERAPEUTIC FORMULATION IN ARTERIOSCLEROSIS

BACKGROUND AND SUMMARY

The present invention relates to a composition containing peroxidic species or oxidation products, its method of preparation, and its use. More specifically, the invention relates to a two-component system of a pharmaceutical formulation which contains: peroxidic species or reaction products resulting from oxidation of an olefinic compound, in a liquid form or in a solution, by an oxygen-containing oxidizing agent; a penetrating solvent; a dye containing a chelated metal; and an aromatic redox compound. The invention also relates to the preparation of the pharmaceutical formulation and its use in treating coronary arteriosclerosis.

Ozone is a triatomic gas molecule and an allotropic form of oxygen. It may be obtained by means of an electrical discharge or intense ultraviolet light through pure oxygen. After the discovery of ozone by Christian Friedrich Schonbein in 1840, six decades passed without any interest in its medical utilization. At the beginning of World War I, Albert Wolf used the gas for the first time therapeutically when it was administered for the topical healing of infected wounds. However, development of medical applications was impeded by the discovery of antibiotic drugs (sulphonamides and penicillins) in the 1920s along with skepticism associated with the internal applications of ozone gas in the field of medicine. For sixty years, ozone clinical research had been limited to European private practice with anecdotal material not published in peer-reviewed journals. Moreover, the popular misconception that ozone is a serious pollutant, the "free radical" theory of disease, and the antioxidant supplement market have comprehensibly prejudiced medical orthodoxy against its use.

Ozone therapy is a misnomer. Ozone is an extremely reactive and unstable gas with mechanisms of action directly related to the by-products that it generates through selective interaction with organic compounds present in the plasma and in the cellular membranes. The selective reaction of ozone with unsaturated olefins occurs at the carbon—carbon double bond, generating ozonides. Ozone is toxic by itself, and its reaction products, ozonides, are unstable and are not therapeutic by themselves.

Hydrogen peroxide ($H_2O_2$), discovered in 1818, is present in nature in trace amounts. Hydrogen peroxide is unstable and decomposes violently (foams) when in direct contact with organic membranes and particulate matter. Light, agitation, heating, and iron all accelerate the rate of hydrogen peroxide decomposition in solution.

Hydrogen peroxide by direct contact ex vivo kills microbes that have low levels of peroxide-destroying enzymes, catalases. For instance, there is no bactericidal effect when hydrogen peroxide is infused into the blood of rabbits infected with peroxide-sensitive E. coli. Moreover, increasing the concentration of peroxide ex-vivo in rabbit or human blood containing E. coli produces no evidence of direct bactericidal activity. The lack of effect of high concentrations of hydrogen peroxide was directly related to the presence of the peroxide-destroying enzyme, catalase. To have any effect, high concentrations of hydrogen peroxide would have to be in contact with the bacteria for significant periods of time. Large amounts of hydrogen peroxide-destroying enzymes, such as catalase, normally present in the blood make it impossible for peroxide to exist in blood for more than a few seconds. One must conclude that hydrogen peroxide introduced into the blood stream by injection or infusion does not directly act as an extracellular germicide in blood or extracellular fluids.

However, hydrogen peroxide does participate in the bactericidal processes within activated macrophage cells. The critical therapeutic criteria for intracellular peroxidation are the selective delivery, absorption and activation of peroxidic carrier molecules into only diseased macrophages, which are believed to be incapable of upgraded catalase and glutathione reductase activity. Infused hydrogen peroxide is a generalized poison whereas targeted intracellular peroxidation is a selective therapeutic tool.

U.S. Pat. No. 4,451,480 to De Villez teaches a composition and method for treating acne. The method includes topically treating the affected area with an ozonized material derived from ozonizing various fixed oil and unsaturated esters, alcohols, ethers and fatty acids.

U.S. Pat. No. 4,591,602 to De Villez shows an ozonide of Jojoba used to control microbial infections.

U.S. Pat. No. 4,983,637 to Herman discloses a method to parenterally treat local and systemic viral infections by administering ozonides of terpenes in a pharmaceutically acceptable carrier.

U.S. Pat. No. 5,086,076 to Herman shows an antiviral composition containing a carrier and an ozonide of a terpene. The composition is suitable for systemic administration or local application.

U.S. Pat. No. 5,126,376 to Herman describes a method to topically treat a viral infection in a mammal using an ozonide of a terpene in a carrier.

U.S. Pat. No. 5,190,977 to Herman teaches an antiviral composition containing a non-aqueous carrier and an ozonide of a terpene suitable for systemic injection.

U.S. Pat. No. 5,190,979 to Herman describes a method to parenterally treat a medical condition in a mammal using an ozonide of a terpene in a carrier.

U.S. Pat. No. 5,260,342 to Herman teaches a method to parenterally treat viral infections in a mammal using an ozonide of a terpene in a carrier.

U.S. Pat. No. 5,270,344 to Herman shows a method to treat a systemic disorder in a mammal by applying to the intestine of the mammal a trioxolane or a diperoxide derivative of an unsaturated hydrocarbon which derivative is prepared by ozonizing the unsaturated hydrocarbon dissolved in a non-polar solvent.

U.S. Pat. No. 5,364,879 to Herman describes a composition for the treatment of a medical condition in a mammal, the composition contains a diperoxide or trioxolane derivative of a non-terpene unsaturated hydrocarbon which derivative is prepared by ozonizing below 35° C. the unsaturated hydrocarbon in a carrier.

Despite the reports on the use of terpene ozonides for different medical indications, terpene ozonides display multiple deficiencies. For example, ozonides of monoterpene, such as myrcene and limonene, flamed out in the laboratory. Consequently, they would be too dangerous to formulate or store.

Furthermore, ozonides of geraniol, a linear monoterpene alcohol, in water or in DMSO did not show any clinical efficacy in three case of viral Varicella Zoster (shingles) and two cases of Herpes Simplex dermatitis.

Coronary heart disease ("CHD") is the single largest killer in the U.S. It affects about 12 million people in this country.

It is responsible for 1 out of 5 deaths, totaling nearly about half a million a year. The disease is caused by a narrowing of the large arteries by plaques made up of blood fats, such as cholesterol, smooth muscle cells, collagen and other proteins, and even calcium deposits. The narrowing of the arteries in turn hamper the supply of blood to the heart muscle. CHD can cause angina, which involves episodes of chest pain due to decrease supply of blood flow and oxygen to the heart muscle. About 6.3 million Americans suffer from angina. CHD can lead to myocardial infarctions, commonly known as heart attacks where tissues in portions of a heart die because of inadequate blood supply. This occurs when one of the coronary arteries becomes completely blocked. Heart attacks affect over 1 million of Americans each year. When the heart muscle is damaged, it has problems pumping blood efficiently, causing congestive heart failure, which affects about 5.6 million Americans. Then, about 4.3 million Americans have heart rhythm disturbances, which are known as arrhythmias.

There is, therefore, a pressing need for new and curative treatments for these diseases.

DETAILED DESCRIPTION

The present invention relates to compositions comprising peroxidic species or reaction products resulting from oxidation of an unsaturated organic compound, in a liquid form or in a solution, by an oxygen-containing oxidizing agent; a penetrating solvent; a chelated dye; and an aromatic redox compound. In one embodiment of the present invention, the essential components include the peroxidic products formed by ozonolysis of an unsaturated alcohol, a stabilizing solvent, metalloporphyrin, and quinone.

The unsaturated organic compound, or the unsaturated olefinic hydrocarbon, for the present invention can be an alkene without a hydroxyl group, or a hydroxyl-containing alkene. Thus, the alkene without a hydroxyl group may be an open-chain unsaturated hydrocarbon, a monocyclic unsaturated hydrocarbon, or a bicyclic unsaturated hydrocarbon. The hydroxyl-containing alkene can be an open-chain unsaturated alcohol, a monocyclic unsaturated alcohol, or a bicyclic unsaturated alcohol.

The unsaturated organic compound may be linear, branched, cyclic, spiral, or complexed with other molecules in its configuration. The unsaturated organic compound may naturally exist in a gaseous liquid or solid state prior to binding with the "activated oxygen."

An open-chain unsaturated hydrocarbons can be: $C_nH_{2n}$, one double bond, n=2–20; $C_nH_{2n-2}$, two double bonds, n=4–20; $C_nH_{2n-4}$, three double bonds, n=6–20; $C_nH_{2n-6}$, four double bonds, n=8–20; $C_{25}H_{40}$, sesterterpene hydrocarbon; or $C_{30}H_{48}$, triterpene hydrocarbon.

A monocyclic unsaturated hydrocarbon can be: $C_nH_{2n-2}$, one double bond+one ring, n=3–20; $C_nH_{2n-4}$, two double bonds+one ring, n=5–20; $C_nH_{2n-6}$, three double bonds+one ring, n=7–20; $C_{25}H_{40}$, sesterterpene hydrocarbon; or $C_{30}H_{48}$, triterpene hydrocarbon.

A bicyclic unsaturated hydrocarbon can be: $C_nH_{2n-4}$, one double bond+two rings, n=4–20; $C_nH_{2n-6}$, two double bonds+two rings, n=6–20; $C_{25}H_{40}$, sesterterpene hydrocarbon; or $C_{30}H_{48}$, triterpene hydrocarbons.

An open-chain unsaturated alcohol can be: $C_nH_{2n}O_m$, one double bond, n=3–20, m=1–4; $C_nH_{2n-2}O_m$, two double bonds, n=5–20, m=1–4; $C_nH_{2n-4}O_m$, three double bonds, n=7–20, m=1–4; $C_nH_{2n-6}O_m$, four double bonds, n=9–20, m=1–4; $C_{25}H_{40}O_m$, m=1–4, sesterterpene alcohols; or $C_{30}H_{48}O_m$, m=1–4, triterpene alcohols.

A monocyclic unsaturated alcohol can be: $C_nH_{2n-2}O_m$, one double bond+one ring, n=3–20, m=1–4; $C_nH_{2n-4}O_m$, two double bonds+one ring, n=5–20, m=1–4; $C_nH_{2n-6}O_m$, three double bonds+one ring, n=7–20, m=1–4; $C_{25}H_{40}O_m$, m=1–4, sesterterpene alcohols; or $C_{30}H_{48}O_m$, m=1–4, triterpene alcohols.

A bicyclic unsaturated alcohol can be: $C_nH_{2n-4}O_m$, one double bond+two rings, n=5–20, m=1–4; $C_nH_{2n-6}O_m$, two double bonds+two rings, n=7–20, m=1–4; $C_{25}H_{40}O_m$, m=1–4, sesterterpene alcohols; or $C_{30}H_{48}O_m$, m=1–4, triterpene alcohols.

Usable unsaturated olefinic hydrocarbons may be unsubstituted, substituted, cyclic or complexed alkenes, hydrazines, isoprenoids, steroids, quinolines, carotenoids, tocopherols, prenylated proteins, or unsaturated fats. The preferred unsaturated hydrocarbons for this invention are alkenes and isoprenoids. The more preferred unsaturated hydrocarbons for this invention are linear isoprenoid alcohols with two to four repeating isoprene groups in a linear chain, such as geraniol, geranylgeraniol, nerol, or linalool.

Isoprenoids are found primarily in plants as constituents of essential oils. While many isoprenoids are hydrocarbons, oxygen-containing isoprenoids also occur such as alcohols, aldehydes, and ketones. In a formal sense, the building block of isoprenoid hydrocarbons may be envisaged as the hydrocarbon isoprene, $CH_2=C(CH_3)-CH=CH_2$, although it is known that isoprene itself is an end-product of isoprenoid biosynthesis and not an intermediate. Isoprenoid hydrocarbons are categorized by the number of isoprene ($C_5H_8$) units they contain. Thus, monoterpenes have 2, sesquiterpenes have 3, diterpenes have 4, sesterterpenes have 5, triterpenes have 6, and tetraterpenes have 8 isoprene units, respectively. Tetraterpenes are much more commonly known as carotenoids.

Limonene and pinene are examples of a monoterpene. Farnesol and nerolidol are examples of a sesquiterpene alcohol. Vitamin $A_1$ and phytol are examples of a diterpene alcohol while squalene is an example of a triterpene. Provitamin $A_1$, known as carotene, is an example of a tetraterpene. Geraniol, a monoterpene alcohol, is liquid in both its oxygen bound and normal states and is safe to living cells.

Based on the total weight of the pharmaceutical formulation, the alkene can vary from about 0.001% to about 30%, preferably from about 0.1% to about 5.0%, and more preferably from about 0.5% to about 3.0%.

The oxygen-containing oxidizing agents for reaction to the unsaturated hydrocarbon may be singlet oxygen, oxygen in its triplet state, superoxide anion, ozone, periodate, hydroxyl radical, hydrogen peroxide, alkyl peroxide, carbamyl peroxide, benzoyl peroxide, or oxygen bound to a transition element, such as molybdenum (e.g. $MoO_5$).

The preferred oxygen-containing oxidizing agents for this invention include ozone, singlet oxygen, and superoxide anion. Ozone is the most preferred oxygen-containing oxidizing agent for binding to the unsaturated hydrocarbon. It is prepared from pure oxygen.

We found that the best method to bind "activated oxygen" to intact geraniol is by ozonation at temperatures between 0–20° C. in the dark in the absence of water or polar solvent. The geraniol "ozonides" were then dissolved and stabilized in 100% dimethylsulfoxide (DMSO) in the dark to prevent premature breakdown of the products. Although not wanting to be bound by any theory, it is believed that the catalytic breakdown of the tetraoxane peroxidic dimer byproduct of geraniol ozonation, which is not an ozonide, occurs inside of cells in the presence of superoxide anion. The final reactive therapeutic agents released are hydrogen peroxide and acetic acid.

Although not wanting to be bound by theory, it is believed that, in general, the reaction between an alkene and ozone in this application proceeds by the Criegee mechanism. According to this mechanism, the initial step of the reaction is a 1,3-dipolar cycloaddition of ozone to the alkene to give a primary ozonide (a 1,2,3-trioxalane). The primary ozonide is unstable and undergoes a 1,3-cycloreversion with the carbonyl compound to give the "normal" ozonide, a 1,2,4-trioxalane.

SCHEME 1

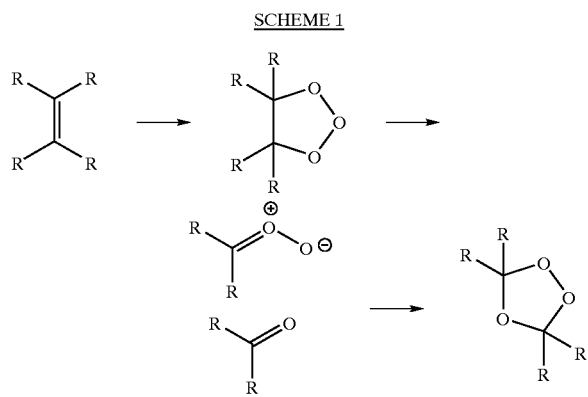

In a side reaction, the carbonyl oxide can enter into a dimerization to give a peroxidic dimer, the 1,2,4,5-tetraoxane.

SCHEME 2

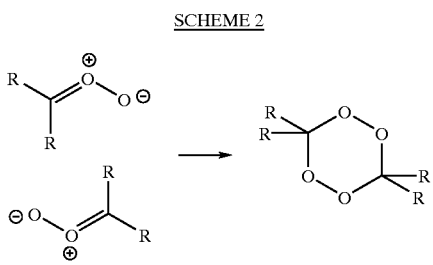

The carbonyl oxide is a strongly electrophilic species, and in the presence of nucleophilic species (e.g. alcohols or water), it undergoes facile nucleophilic addition to give a 1-alkoxyhydroperoxide. Under certain conditions, the 1-alkoxyhydroperoxide can undergo further reaction to give carboxylic acid derivatives.

SCHEME 3

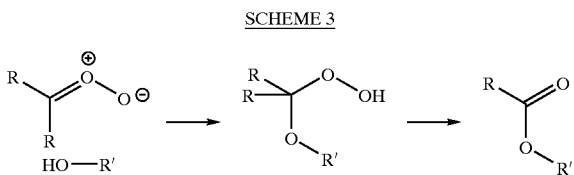

Again, not wanting to be bound by theory, it is believed that during the ozonolysis of the alcohol-containing alkene in the present invention, it is reasonable to expect that three major types of peroxidic products will be present: the normal ozonide, the carbonyl tetraoxane dimer, and the 1-alkoxyhydroperoxide. In the presence of water, some of these peroxidic products may also lead to the presence of organic peracids in the crude product mixture.

The present invention involves the use of DMSO to "stabilize" the initial products of the ozonolysis. Similarly, not wanting to be bound by any theozy, it is believed that the stabilization is most likely a simple solvation phenomenon. However, dimethyl sulfoxide is known to be a nucleophile in its own right. Its participation is also possible as a nucleophilic partner in stabilizing reactive species (for example, as dimethylsulfoxonium salts).

The penetrating solvent for the oxygen-bound unsaturated hydrocarbon may be an emollient, a liquid, a membrane, a micelle, a plasma or a vapor.

Usable penetrating solvents are water, fats, sterols, lecithins, phosphatides, pH-buffered saline, ethanol, propylene glycol, dimethyl sulfoxide, methylsulfonylmethane, and polyvinylpyrrolidine. The preferred penetrating solvents include dimethylsulfoxide, polyvinylpyrrolidine, and pH-buffered saline. The most preferred penetrating solvent includes dimethylsulfoxide.

Based on the total weight of the pharmaceutical formulation, the penetrating solvent can vary from about 50% to about 99%, preferably from about 90% to about 98%, and more preferably from about 95% to about 98%.

The "stabilized" peroxidic molecule and its penetrating solvent have been made from components currently used in production regulated by the Food and Drug Administration ("FDA"). These ingredients are the subject of Drug Master Files, Drug Monographs, are found in the USP/NF, or are Generally Recognized As Safe ("GRAS"). The superoxide generating dye and perpetuating agent, also biologically compatible, probably conveniently form a molecular complex.

The other components of the pharmaceutical formulation can include the metalloporphyrin and quinone. The propensity of metalloporphyrins to sensitize oxygen under photochemical excitation is well documented as is the propensity of ferroporphyrins and copper porphyrins to bind oxygen-containing systems.

Researchers of photodynamic therapy have known that the superoxide dye and the perpetuator selectively absorb into infected and dysplastic cells. These diseased cells are fortuitously both catalase deficient. The electronic activation of the dye and perpetuator simply requires a milli-volt AC pulse. This requisite pulse is conveniently provided by a beating heart. Moreover, normal cells are not harmed.

Usable dyes, include natural or synthetic dyes. Examples include porphyrins, rose bengal, chlorophyllins, hemins, porphins, corrins, texaphrins, methylene blue, hematoxylin, eosin, erythrosin, flavinoids, lactoflavin, anthracene dyes, hypericin, methylcholanthrene, neutral red, and fluorescein.

For this invention, the preferred dyes can be any natural or synthetic porphyrin, hematoporphyrin, chlorophyllin, rose bengal, their respective congeners, or a combination thereof. The most preferred dyes are naturally occurring porphyrins, such as hematoporphyrin, and rose bengal.

Based on the total weight of the pharmaceutical formulation or composition, the dye can vary from about 0.1% to about 30%, preferably from about 0.5% to about 5%, and more preferably from about 0.8% to about 1.5%.

The dye may be responsive to photon; laser; ionizing radiation; phonon; electrical cardiac electroporation; magnetic or plasma pulse; or continuous flow excitation.

The aromatic redox compound includes any substituted or unsubstituted benzoquinone, naphthoquinone, or anthroquinone. The preferred aromatic redox compound includes benzoquinone, methyl-benzoquinone, naphthoquinone, and methyl-naphthoquinone. The most preferred aromatic redox compound includes substituted or unsubstituted benzoquinone and naphthoquinone.

Based on the total weight of the pharmaceutical formulation, the aromatic redox compound can vary from about 0.01% to about 20.0%, preferably from about 0.1% to about 10%, and more preferably from about 0.1% to about 0.5%.

Useful electron donors for this invention include plasma, an electrical current, ascorbate, and germanium sesquioxide. Preferred electron donors include ascorbate and germanium sesquioxide. The most preferred electron donor is ascorbate in any salt form.

Based on the total weight of the pharmaceutical formulation, the electron donor can vary from about 0.01% to about 20%, preferably from about 1% to about 10%, and more preferably from about 1% to about 5%.

In order to obtain a biological effect in vivo, it is necessary to infuse an ozonolysis peroxidic tetraoxane product of a terpene alcohol, rather than an ozonide, in conjunction with a superoxide generating metallo-porphyrin dye an aromatic quinone.

Although not wanted to be bound by any theory, it is postulated that the preferred pharmaceutical formulation is a combination of biochemical agents that induce recycling autocatalytic oxidation in infected or dysplastic macrophages. The recycling autocatalytic oxidation stimulates targeted apoptosis (cell suicide) through peroxidation.

The pharmaceutical formulation of this invention as described in Example 3B ("Terphorone") was utilized to treat patients with coronary artery disease. For the patient studies, the dose was case specific. Generally, it was 1.0 cc of Terphorone per 70 kg of body weight. The schedules could be 2 infusions monthly for 6 months, then 2 infusions every 3 months for 2 years, and the route of administration was preferably i.v., although other routes of administration were possible.

EXAMPLE 1

Ozonolysis of an alkene may be carried out either in a solvent or neat. In either case, the cooling of the reaction mixture is critical in avoiding explosive decomposition of the peroxidic products of the reaction.

The following general procedure is typical for the ozonolysis of a liquid alkene.

A 1-liter flask fitted with a magnetic stirrer is charged with the alkene (2 moles), and the apparatus is weighed. The flask is surrounded by a cooling bath (ice-water or ice-salt). Once the contents are cooled below 5° C., stirring is begun and a stream of ozone in dry oxygen (typically 3% ozone) is passed through the mixture. It is advantageous to disperse the ozonated oxygen through a glass frit, but this is not necessary for a stirred solution. Periodically, the gas stream is stopped, and the reaction flask is weighed or the reaction mixture is sampled. The gas stream is then re-started.

Once the mass of the reaction flask shows sufficient weight gain, or once the proton magnetic resonance ("$H^1$ NMR") spectrum of the reaction mixture shows the desired reduction in the intensity of the olefinic proton resonances (usually about 50%), the gas flow is stopped.

The ozonolysis may be carried out as above, substituting a solution of the alkene in a solvent non-reactive towards ozone such as saturated hydrocarbons or chlorinated hydrocarbons.

The ozonolysis may be carried out as above, with or without solvent, substituting an alkenol for the alkene without affecting the reaction in any substantive manner.

The reaction mixture is then poured slowly into the cooled penetrating solvent.

EXAMPLE 2

A preferred pharmaceutical formulation of the present invention was prepared as follows:

(1) Sparging an ozone/pure oxygen gas mixture of 120 mg/L up through an alkadiene alcohol, 3,7-dimethyl-2,6-octadien-1-ol (geraniol), at 1 Liter of gas per hour;

(2) Maintaining the temperature of the reaction around 5° C.;

(3) Removing small aliquots of reaction product hourly and measuring by $H^1$ NMR the formation of the peroxidic species or reaction products;

(4) Stopping the reaction when more than about 50% of the available unsaturated bonds have been reacted;

(5) Diluting the product mixture dimethylsulfoxide (1:10) to give a solution or dispersion; and (6) Prior to use in the target biological system, a mixture of hematoporphyrin, rose bengal, and methylnaphthoquinone dry powders was added to the solution or dispersion in sufficient quantity to create a concentration of 20 micromolar of each component dispersed therein when delivered to the target biological system by saline intravenous infusion. Optionally, ascorbate could be added to the formulation prior to use.

EXAMPLE 3

Two preferred formulations are as follows:

| WEIGHT % | A. INGREDIENT |
|---|---|
| 0.54* | Tetraoxane dimer of acetal peroxide from ozonization of geraniol. |
| 98.00 | DMSO |
| 0.83 | Hematoporphyrin |
| 0.24 | Methylnaphthoquinone |
| 0.39 | Rose Bengal |

*Determined by mass spectroscopy.

| WEIGHT % | B. INGREDIENT |
|---|---|
| 0.54* | Tetraoxane dimer of acetal peroxide from ozonization of geraniol. |
| 98.00 | DMSO |
| 0.83 | Hematoporphyrin |
| 0.24 | Methylnaphthoquinone |
| 0.39 | Chlorophyllin Sodium-Copper Salt |

*Determined by mass spectroscopy.

EXAMPLE 4

The pharmaceutical formulation of the present invention can be incorporated into a premixed solvent. This formulation is very stable and exhibited the same minimal toxicity profile and clinical efficacy after more than a year of storage. Moreover, to avoid the stability issue entirely, the formulation can be packaged in a two-vial system. More specifically, the package consists of a small box containing the following:

(1) Vial of liquid phase containing: (a) the peroxidic species or reaction products resulting from oxidation of an alkene in a liquid form or in a solution, by an oxidizing agent; and (b) a penetrating solvent.

(2) Vial of relatively dry solid relatively dry phase containing: (a) a dye containing a chelated divalent or trivalent metal; and (b) an aromatic redox compound.

(3) An optional mixing needle.

(4) An optional package insert.

The liquid phase is introduced into the vial of solid phase and then shaken to mix. The pharmaceutical formulation of the present invention is thus reconstituted at the patient's side. Thus, the stability of the formulation is greatly enhanced.

EXAMPLE 5

A 63-year old Caucasian female with a medical history of a two-vessel coronary artery bypass graft ("CABG") in 1996, followed by repeat of mammary artery graft in March 2000. Her left main coronary artery stenosis could not be addressed at the time of the second surgery, as her vessels were deemed too small to bypass or stent. Within six weeks of mammary artery graft, the patient was advised that this graft had re-blocked secondary to "scar formation". The patient was scheduled for internal and external X-irradiation of coronary grafts to control scar formation. The patient is a known keloid scar former. The vein graft donor site from the left forearm had formed extensive keloid from wrist to elbow, approximately 10.5 cm.×1.5 cm. The patient opted to consider bio-oxidative non-invasive treatment. Prior to infusions of the Terphorone, the patient reported using up to 30 sublingual nitroglycerine ("NTG") sublingual tablets per week. She averaged a trip to the emergency room every two to three weeks for i.v. NTG infusion to resolve angina. These trips included three to four day follow-up stays in the I.C.U. Since about 8 months ago, the patient has received six doses of the Terphorone. The dose was 1 cc of Terphomone diluted in 100 cc of sterile normal saline, infused over 20 minutes. Her sublingual angina therapy was down to one per week, with most weeks requiring no NTG at all. She has not been to the hospital for i.v. anti-angina NTG infusion since receiving her first infusion of the preferred formulation described in Example 3B. Moreover, the patient's keloid from her graft donor site on the left forearm virtually disappeared following her first two doses of the Terphorone.

EXAMPLE 6

A 62-year old Caucasian male with a medical history of multiple-vessel coronary artery bypass graft ("CABG") surgery twice in 1994. Increasing angina brought the patient to treatment in October 1999. The patient required an NTG patch (0.4 mg/hr) daily to relieve both stable and unstable angina. Physical activity was limited to nearly zero at that time. The patient's cardiologist recommended another repeat bypass at that time. Since October 1999, the patient has received 20 i.v. 0.5 cc doses of the Terphorone which formulation is described in Example 3B. The dosage was 0.5 cc progressing to 1.0 cc in 0.1 cc steps, diluted in 100 cc sterile normal saline, infused over 20 minutes. The patient's angina has totally subsided both at rest and with routine exercise. He no longer requires an NTG patch. He now plays golf and walks the course four to six times per week. The only setback this patient has had during his course of oxidative therapy came when his cardiologist diagnosed him with atrial fibrillation of new onset in early 2000. The cardiologist placed the patient on Coumadin (anticoagulant). Terphorone treatment was terminated temporarily, due to its contraindication with Coumadin therapy. When the atrial fibrillation resolved, the patient was weaned off of Coumadin and Terphorone treatments were resumed. The patient is symptom free with a normal cardiac conduction at this time.

EXAMPLE 7

A 50-year old Caucasian male first seen in the emergency room with chest pain in 1996. The EKG showed nonspecific ST-T wave changes. The patient was scheduled for coronary angiogam with angioplasty, but he refused the procedure. The subjective complaint made by the patient was primarily severe chest pain on exertion. His job required climbing ladders up three story buildings for the inspection of air conditioning equipment. The patient complained that chest pain was so severe upon reaching the top of the buildings that he would have to rest in a supine position for varying amounts of time before resuming work. The angina was relieved with sublingual NTG. Since about 11 months ago, the patient has received six intravenous doses of Terphorone. The dosage was 0.5 cc progressing to 1.0 cc in 0.1 cc steps, diluted in 100 cc sterile normal saline, infused over 20 minutes. Angina has completely subsided, even on extreme exertion. The patient continues to accomplish the same work he was doing prior to treatment, now without incident. He has not required sublingual NTG since initiation of Terphorone therapy.

EXAMPLE 8

A 47-year old Caucasian male had a history of multiple M.I.s. He reported having an M.I. every six months to one year for the five years leading up to his CABG (×4) in 1996. The patient was discharged from the military under full disability secondary to the cardiac condition. The patient required NTG paste on his chest during sex leading up to and following CABG surgery. Before being examined for this experiment, the patient's cardiologist at a hospital had recommended a heart transplant. He had five or six Thallium stress tests performed on him in the year preceding his participation in this trial. All of these tests were positive for multiple vessel disease. Since about 1.5 years ago, the patient has received eight doses of Terphorone. The dosage was 0.5 cc progressing to 1.0 cc in 0.1 cc steps, diluted in 100 cc sterile normal saline, infused over 20 minutes. He no longer requires NTG paste during sex. He is able now to do exertion, such as mowing his lawn, without chest pain. His cardiologist still maintains that the he needs a heart transplant. The patient's only medications at this time are a long-acting vasodilator once a day by mouth and a low dose ACE inhibitor once daily.

EXAMPLE 9

An 89-year old Caucasian male had a history of transient ischemic attacks. He had right carotid artery arteriosclerosis, reported to be an 85% blockage by direct imaging. The patient had been in atrial fibrillation for approximately one year and was taking Rhythmol. He also reported extreme lethargy on a daily basis. He reported some disorientation on occasion and had had some falls in the past. The vascular surgeon recommended immediate carotid endarterectomy. The patient opted for alternative non-invasive treatment. Since September 2000, the patient has received 4 doses of Terphorone. The dosage was 0.5 cc progressing to 1.0 cc in 0.1 cc steps, diluted in 100 cc sterile normal saline, infused over 20 minutes. His general stamina has increased by at least 50%, according to his caretaker. The patient was placed on a 24 hour Holter monitor two weeks following his first two Terphorone infusions. His atrial fibrillation had resolved. Although he was weaned off of his Rhythmol, the atrial fibrillation had not returned. The patient has not had a transient ischemic attack since initiation of Terphorone therapy. In early November 2000, he went on a seven-day cruise with his family without incident.

EXAMPLE 10

Ozone at a concentration of 120 mcg/ml at ⅛ L/min was sparged up through 100 ml of 100% myrcene liquid at 5° C., and the vapor was allowed to enter the atmosphere. Static electricity from the chemist set off an explosive flame in the vapor.

Ozonated limonene was created by the same method with precautions against spark generation. The ozonide product was stored in a closet at room temperature in a sealed brown bottle overnight. The next morning the chemist and pharmacist saw fine glass powder and a syrupy chemical splashed inside the closet.

EXAMPLE 11

Ozone (120 micrograms/ml) was bubbled up through 1 L of neat geraniol at 5° C. for 48 hours. The reaction products were diluted 1:9 with DMSO to give a product mixture.

The mixture at 3% was administered intravenously to a patient suffering from Herpes (Varicella) Zoster daily for 3 consecutive days. There was no observable effect or improvement on the patient's Herpes (Varicella) Zoster.

The invention may be embodied in other specific forms without departing from the spirit or essential characteristics thereof. The present embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. An article of manufacture comprising:
   a first container containing a liquid phase, the liquid phase comprising:
      peroxidic species or reaction products resulting from oxidation of menthol or an alkene by a mixture of ozone and oxygen, wherein the alkene comprises α-terpineol, citronellol, nerol, linalool, phytol, geraniol, perillyl alcohol, geranylgeraniol or farnesol;
      a penetrating solvent, wherein the penetrating solvent comprises dimethylsulfoxide, sterol, lecithin, propylene glycol, or methylsulfonylmethane; and
   a second container containing a solid phase, the solid phase comprising:
      a dye containing a chelated divalent or trivalent metal, wherein the dye comprises porphyrin, rose bengal, chlorophyllin, hemin, corrins, texaphrin, methylene blue, hematoxylin, eosin, erythrosin, lactoflavin, anthracene dye, hypericin, methylcholanthrene, neutral red, or fluorescein; and
      an aromatic redox compound, wherein the redox compound comprises substituted or unsubstituted benzoquinone, naphthoquinone, or anthroquinone,
   wherein the liquid phase and the solid phase in combination comprise about 0.001% to about 30% by weight of the peroxidic species or reaction products resulting from oxidation of menthol or the alkene, from about 50% to about 99% by weight of the penetrating solvent, from about 0.1% to about 30% by weight of the dye, and from about 0.01% to about 20% by weight of the aromatic redox compound.

2. The article of manufacture of claim 1, wherein the alkene is in a liquid form, in a solution, or in a dispersion.

3. The article of manufacture of claim 1, wherein the mixture of ozone and oxygen contains singlet oxygen, oxygen in its triplet state, superoxide anion, periodate, hydroxyl radical, peroxide, or oxygen bound to a transition element.

4. The article of manufacture of claim 1, wherein the mixture of ozone and oxygen comprises predominantly ozone.

5. The article of manufacture of claim 1, wherein the penetrating solvent is a liquid, micelle membrane, emollient, plasma, or vapor.

6. The article of manufacture of claim 1, wherein the penetrating solvent is dimethylsulfoxide.

7. The article of manufacture of claim 1, wherein the dye comprises porphyrin or rose bengal.

8. The article of manufacture of claim 1, wherein the dye can be activated by an energy source.

9. The article of manufacture of claim 8, wherein the energy source comprises photon.

10. The article of manufacture of claim 8, wherein the energy source comprises laser or ionizing radiation.

11. The article of manufacture of claim 1, wherein the metal comprises iron.

12. The article of manufacture of claim 1, wherein the metal comprises copper, manganese, tin, magnesium, or strontium.

13. The article of manufacture of claim 1 further comprising an electron donor.

14. The article of manufacture claim 13, wherein the electron donor comprises ascorbic acid or a pharmaceutical salt thereof.

15. The article of manufacture of claim 13, wherein the electron donor comprises germanium sesquioxide or electrical current, wherein the electrical current is applied to the combination of the liquid phase of the first container and the solid phase of the second container after mixing.

16. A method for treating a patient with coronary arteriosclerosis comprising:
   administering to the patient an effective amount of a pharmaceutical formulation comprising:
   peroxidic species or reaction products resulting from oxidation of menthol or an alkene by an oxygen-containing oxidizing agent, wherein the alkene comprises α-terpineol, citronellol, nerol, linalool, phytol, geraniol, perillyl alcohol, geranylgeraniol or farnesol, and wherein the peroxidic species or reaction products resulting from oxidation of menthol or the alkene is from about 0.001% to about 30% by weight of the pharmaceutical formulation;
   a penetrating solvent, wherein the penetrating solvent comprises dimethylsulfoxide, sterol, lecithin, propylene glycol, or methylsulfonylmethane, and wherein the penetrating solvent is from about 50% to about 99% by weight of the pharmaceutical formulation;
   a dye containing a chelated divalent or trivalent metal, wherein the dye comprises porphyrin, rose bengal, chlorophyllin, hemin, corrins, texaphrin, methylene blue, hematoxylin, eosin, erythrosin, lactoflavin, anthracene dye, hypericin, methylcholanthrene, neutral red, or fluorescein, and wherein the dye is from about 0.1% to about 30% by weight of the pharmaceutical formulation; and
   an aromatic redox compound, wherein the redox compound comprises substituted or unsubstituted benzoquinone, naphthoquinone, or anthroquinone, and wherein the aromatic redox compound is from about 0.01% to about 20% by weight of the pharmaceutical formulation.

17. The method of claim 16, wherein the alkene is in a liquid form, in a solution, or in a dispersion.

18. The method of claim 16, wherein the mixture of ozone and oxygen contains singlet oxygen, oxygen in its triplet state, superoxide anion, periodate, hydroxyl radical, peroxide, or oxygen bound to a transition element.

19. The method of claim 16, wherein the mixture of ozone and oxygen comprises predominantly ozone.

20. The method of claim 16, wherein the penetrating solvent is a liquid, micelle membrane, emollient, or vapor.

21. The method of claim 16, wherein the penetrating solvent is dimethylsulfoxide.

22. The method of claim 16, wherein the dye comprises porphyrin or rose bengal.

23. The method of claim 16, wherein the metal comprises iron.

24. The method of claim 16, wherein the metal comprises copper, manganese, tin, magnesium, or strontium.

25. The method of claim 16, further comprising an electron donor.

26. The method of claim 16, wherein the electron donor comprises ascorbic acid or a pharmaceutical salt thereof.

* * * * *